United States Patent [19]

Plueddemann

[11] Patent Number: 4,719,262

[45] Date of Patent: Jan. 12, 1988

[54] ORGANOSILICON PRIMER COMPOSITIONS

[75] Inventor: Edwin P. Plueddemann, Midland, Mich.

[73] Assignee: Dow Corning Corporation, Midland, Mich.

[21] Appl. No.: 922,380

[22] Filed: Nov. 28, 1986

Related U.S. Application Data

[62] Division of Ser. No. 844,057, Mar. 26, 1986, Pat. No. 4,659,851.

[51] Int. Cl.$^4$ .................................................. C08F 8/00
[52] U.S. Cl. ................................... 525/105; 525/100; 525/106; 528/31; 528/32; 556/431; 556/440; 556/443; 556/444
[58] Field of Search .................. 525/100, 105, 106; 528/32, 31; 556/431, 440, 444, 443

[56] References Cited

U.S. PATENT DOCUMENTS

| | | | |
|---|---|---|---|
| 3,306,800 | 2/1967 | Pleuddemann | 525/106 |
| 3,369,006 | 2/1968 | Brown | 260/80 |
| 3,472,888 | 10/1968 | Bazouin et al. | 260/448.8 |
| 4,208,319 | 6/1980 | August et al. | 525/100 |
| 4,593,072 | 6/1986 | Keogh | 525/106 |

FOREIGN PATENT DOCUMENTS 57469 12/1985 Japan.
1058866 2/1967 United Kingdom.

OTHER PUBLICATIONS

D. F. Peppard, Journal of the American Chemical Society, vol. 68 (1946), pp. 70–72, *Preparation and Synthetic Applications of Alkyl Chlorosilicates.*
D. F. Peppard, Journal of the American Chemical Society, vol. 68 (1946), pp. 73–75, *Alcoholysis Reactions of Alkyl Silicates.*

*Primary Examiner*—Melvyn I. Marquis
*Attorney, Agent, or Firm*—Robert Spector

[57] ABSTRACT

This invention provides novel silanes and bis-silylhydrocarbons that contain a plurality of silicon-bonded alkoxy groups and at least one substituent that is bonded to silicon through oxygen and contains at least four carbon atoms, two of which form a terminal group of the formula $CH_2=CH-$. A preferred class of these compounds will cohesively bond polyorganosiloxane elastomers and resins to both organic and inorganic substrates.

10 Claims, No Drawings

ORGANOSILICON PRIMER COMPOSITIONS

This is a divisional of co-pending application Ser. No. 844,057 filed on Mar. 26, 1986 now U.S. Pat. No. 4,659,851.

BACKGROUND OF THE INVENTION

1. Field of the Invention

This invention relates to novel organosilicon compounds. More particularly, this invention relates to organosilicon compounds containing one or two silicon atoms, at least two silicon-bonded alkoxy groups and at least one group that is bonded to silicon through oxygen and contains ethylenic unsaturatiion at a terminal position.

2. Description of the Prior Art

Certain types of silanes and other organosilicon compounds containing ethylenically unsaturated radicals bonded to silicon by means of an oxygen atom have been disclosed in the prior art.

Reaction products of ethylenically unsaturated epoxide compounds with chlorosilanes or bis-trichlorosilhydrocarbon compounds of the general formula $Cl_3SiQSiCl_3$ where Q represents alkylene, alkenylene, arylene or alkarylene are disclosed in U.S. Pat. No. 3,369,006, which issued to Brown on Feb. 13, 1968. All of these reaction products contain a silicon-bonded chlorinated alkenyloxy radical of the general formula $YCHCLCH_2OSi$, where Y represents an ethylenically unsaturated organic radical containing carbon, hydrogen and, optionally, oxygen and halogen.

1-alkenyloxysilanes wherein an ethylenically unsaturated carbon atom is bonded to an oxygen atom that is in turn bonded to silicon are disclosed in U.S. Pat. No. 3,472,888, which isssued to Bazouin et al on Oct. 14, 1969, and in British Patent No. 1,058,866, which issued on Feb. 15, 1967. Bazouin describes vinyloxysilanes that are reaction products of a chlorosilane, represented by the formula $R_nSiCl_{(4-n)}$, with the enol form of an aldehyde or ketone, the enol compound being represented by the general formula $R'R''C=CR'''OH$. The products of this reaction exhibit the general formula $R_nSiO(R''')C=CR'R''_{4-n}$, where R represents a monovalent organic radical, and R', R" and R''' each represent a hydrogen atom or a monovalent organic radical that is free of reactive substituents. The compounds described in the British patent can be represented by the same general formula used for Bazouin's compounds, with the proviso that the radicals represented by R', R" and R''' optionally contain ethylenic unsaturation which is reactive with carbon monoxide. The compounds of the British patent are prepared by reacting a terminally unsaturated hydrocarbon with (1) a silane containing a silicon-bonded hydrogen atom and (2) carbon monoxide.

The preparation of allyloxytrimethoxysilane is described by D. F. Peppard in articles that begin on pages 70 and 73 of volume 68 of the Journal of the American Chemical Society. The articles were published in 1946. The silane was prepared by reacting allyl alcohol with trimethoxychlorosilane in the presence of pyridine.

SUMMARY OF THE INVENTION

An objective of this invention is to provide novel silanes and bis-silylhydrocarbons that contain a plurality of silicon-bonded alkoxy groups and at least one substituent that is bonded to silicon through oxygen and contains at least four carbon atoms, two of which form a terminal group of the formula $CH_2=CH—$.

A second objective of this invention is to provide novel organosilicon compounds that will cohesively bond polyoganosiloxane elastomers and resins to inorganic and organic substrates.

DETAILED DESCRIPTION OF THE INVENTION

The novel compounds of this invention include silanes of the general formulae

$(R^1O)_n(R^2O)_{4-n-p}R^3_pSi$  Formula 1 and

$R^4[OSi(OR^2)_{3-p}R^3_p]_2$  Formula 2 and organosilicon compounds of the general formulae

$(R^1O)_n(R^2O)_{3-n}SiR^5Si(OR^1)_r(OR^2)_{3-r}$  Formula 3 and

$R^4[OSi(OR^2)_2R^5Si(OR^2)_3]_2$  Formula 4 where $R^1$ represents a radical selected from the group consisting of

$CH_2=CHCH_2R^6$,  Formula 5

$CH_2=CHR^6OR^7—$,  Formula 6

$CH_2=CHR^6OC(O)R^8$  Formula 7

$CH_2=CHR^9C(O)OR^7$,  Formula 8 and

$(CH_2=CHR^6O)_2R^{10}$;  Formula 9

$R^2$ represents an alkyl radical containing from 1 to 4 carbon atoms;

$R^3$ represents a monovalent hydrocarbon or fluorinated hydrocarbon radical; $R^4$ represents a radical selected from the group consisting of

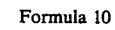

$CH_2=CHR^{10}<$,  Formula 10

$CH_2=CHR^6OR^{10}<$,  Formula 11

$CH_2=CHR^6OC(O)R^{10}<$,  Formula 12 and

$CH_2=CHR^9C(O)OR^{10}<$,  Formula 13

$R^5$ represents hydrocarbylene containing at least 2 carbon atoms;

$R^6$ represents a hydrocarbylene or substituted hydrocarbylene radical where the substituent is hydroxyl or alkoxy;

$R^7$ is selected from the same group as $R^6$, or represents an allyloxy-substituted hydrocarbylene radical with the proviso that $R^7$ contains at least 2 carbon atoms;

$R^8$ is selected from the same group as $R^6$;

$R^9$ represents a single bond or a radical selected from the same group as $R^6$;

$R^{10}$ represents a trivalent hydrocarbon radical;

n is 1 or 2;
p is 0 or 1;
r is 0 or 1; and
$4-n-p$ is at least 2.

In preferred embodiments of the present compounds, $R^2$ is methyl or ethyl, $R^3$ represents an alkyl, haloalkyl or phenyl, $R^5$ and $R^7$ each contain from 2 to 10 carbon atoms, $R^8$ contains from 1 to 10 carbon atoms, $R^9$ represents a single bond, alkylene containing from 1 to 10 carbon atoms, cycloalkylene or phenylene, and $R^{10}$ contains from 3 to 10 carbon atoms.

Compounds of this invention wherein $R^2$ and $R^3$ of the foregoing formulae 1–4 are methyl, $R^5$ is ethylene, n is 1 or 2, p is 0 or 1 and r is 0 constitute a preferred class that is particularly useful as either primers or adhesion promoters for cohesively bonding polyorganosiloxane elastomers to a variety of substrates. The silicon-bonded hydrocarbon radicals of the polyorganosiloxane are preferably methyl.

The organosilicon compounds of this invention can be defined as silanes, alpha, omega-disilylalkanes, -disilylcycloalkanes and -disilylarenes that contain at least two silicon-bonded alkoxy groups per molecule and at least one substituent corresponding to $R^1$ in the foregoing formulae 1 and 3 or one substituent corresponding to $R^4$ in formulae 2 and 4.

$R^1$ is bonded to an oxygen atom that is in turn bonded to silicon and contains at least four carbon atoms, two of which form an ethylenically unsaturated terminal group of the formula $CH_2=CH-$. The remainder of $R^1$ is composed of hydrogen and, optionally, oxygen atoms. In one embodiment $R^1$ contains two unsaturated terminal groups.

The substituent identified as $R^4$ in the preceding formulae 2 and 4 is identical to $R^1$, except for the fact that it is trivalent and bonded to two silicon-bonded oxygen atoms.

The four embodiments of the $R^1$ and $R^4$ substituents defined in the preceding formulae 5 through 12 are described in detail hereinafter. In these embodiments $R^1$ is the residue remaining following removal of a hydroxyl group from one of five classes of organic compounds. $R^4$ is the residue remaining following removal of two hydroxyl groups from the same classes of compounds.

The five classes of organic compounds included within the definitions of the $R^1$ and $R^4$ substituents are (1) terminally unsaturated alcohols, (2) phenols containing a terminally unsaturated aliphatic hydrocarbon radical as a substituent, (3) ethers derived from the reaction of either (1) or (2) with either a saturated polyhydric alcohol or a polyhydric phenol, (4) esters derived from the reaction of a terminally unsaturated carboxylic acid with either a saturated polyhydric alcohol or a polyhydric phenol and (5) esters derived from the reaction of either (1) or (2) with a saturated aliphatic, a saturated cycloaliphatic or an aromatic hydroxycarboxylic acid.

The compounds of this invention can be prepared by reacting one of these five classes of organic compounds with an alkoxysilane or a bis-silylhydrocarbon containing silicon-bonded alkoxy groups. The reaction products contain at least two alkoxy groups per silicon atom.

If the aforementioned organic and organosilicon compounds are reacted in substantially equimolar quantities the resultant compound of this invention will be represented by the foregoing formula 1 or 3, depending upon whether the organosilicon reactant is a silane or a bis-trialkoxysilylhydrocarbon. When one mole of an organic compound containing two or more hydroxyl groups is present for every two moles of organosilicon compound, the reaction product will conform to the foregoing formula 2 or 4.

In one embodiment, referred to hereinafter as A, $R^1$ is defined as $CH_2=CHCH_2R^6-$, and $R^4$ is defined as $CH_2=CHR^{10}=$. In these formulae $R^6$ is a hydrocarbylene radical that is either unsubstituted or contains at least one hydroxyl and/or alkoxy group and $R^{10}$ is a trivalent hydrocarbon radical. $R^6$ preferably represents unsubstituted alkylene containing from 1 to 10 or more carbon atoms, hydroxyl substituted alkylene, hydroxyl substituted alkylene, unsubstituted cyclohexylene, unsubstituted phenylene, hydroxyl- or alkoxy substituted phenylene or the residue remaining following removal of one of the two terminal hydroxyl groups from a hydroxyl terminated polybutadiene molecule of the formula Formula 16

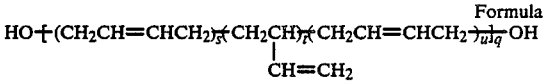
$$|$$
$$CH=CH_2$$

where q represents an integer from 10 to about 100, inclusive, the value of u is greater than 0 and the sum of s, t and u is 1. Preferably q is between 50 and 60 and u is between 0.5 and 1.0.

In embodiment A, $R^1$ and $R^4$ represent the residue remaining following removal of one and two hydroxyl groups, respectively, from either (1) a terminally unsaturated alcohol or (2) a phenol containing a terminally unsaturated hydrocarbon radical as a substituent. As used in this specification the term 'terminally unsaturated' implies the presence of a hydrocarbon radical that includes a $CH_2=CH-$ grouping at a terminal position.

Terminally unsaturated monohydric alcohols useful for preparing the present compounds contain at least 4 carbon atoms, and include but are not limited to 3-buten-1-ol, 3-butene-2-ol, 2-methyl-3-butene-2-ol, 5-hexen-1-ol, 9-decene-1-ol, 17-octadecen-1-ol and the isomeric allyl substituted cyclohexanols.

Terminally unsaturated polyhydric alcohols or partial ethers thereof can be substituted for a monofunctional alcohol. It will be understood that a terminally unsaturated alcohol containing at least two hydroxyl groups or a phenol containing at least two hydroxyl groups and a terminally unsaturated hydrocarbon radical as substituents must be used to prepare compounds of this invention corresponding to the foregoing formula 2 or 4.

Monohydric, terminally unsaturated phenols include the isomeric allyl phenols and cresols. The definition of $R^1$ for embodiment A encompasses residues of diphenols, such as hydroquinone, having as a substituent on the phenyl ring a terminally unsaturated hydrocarbon radical containing at least 3 carbon atoms. One of the hydroxyl groups of the diphenol can be reacted to form an ether or ester as, for example, in eugenol.

In a second embodiment of the present compounds, referred to hereinafter as embodiment B, $R^1$ is defined as $CH_2=CHR^9C(O)OR^7$ —and $R^4$ is defined as $CH_2=CHR^9C(O)OR^{10}<$. $R^7$ is selected from the same group of hydrocarbylene radicals as defined hereinabove for $R^6$ or $R'$ can represent an allyloxy substituted hydrocarbylene radical, with the proviso that $R^7$ contains at least two carbon atoms. $R^9$ is also selected from the same group of radicals as $R^6$ or it can represent a single bond and $R^{10}$ represents a trivalent hydrocarbon radical.

For the compounds of embodiment B, $R^1$ and $R^4$ represent the residues remaining following removal of one and two hydroxyl groups, respectively, from the alcohol portion of an ester derived from the reaction of a terminally unsaturated carboxylic acid with either (1) a saturated aliphatic or saturated cycloaliphatic alcohol containing at least two hydroxyl groups or, (2) a phenol containing at least two hydroxyl groups. Suitable alcohols and phenols can be represented by the formula $HOR^7OH$. Preferably $R^9$ represents a single bond and $R^7$ represents unsubstituted alkylene containing from 2 to 10 carbon atoms, hydroxyl substituted alkylene containing from 3 to 10 carbon atoms or phenylene, this preference being based on the availability of the corresponding alcohols and phenols.

Representative polyhydric alcohols include but are not limited to ethylene glycol, the isomeric propylene glycols, glycerol, 1,1,1-trimethylolpropane, 1,4-cyclohexanediol and other alcohols containing at least two hydroxyl groups per molecule and up to 20 or more carbon atoms. Partially etherified polyhydric alcohols containing three or more hydroxyl groups, at least two of which are unreacted, are also suitable precursors for the alcohol portion of compounds corresponding to embodiment B. Representative polyhydroxylated phenols include the aforementioned hydroquinone and resorcinol.

It will be understood that the alcohol or phenol used to prepare the ester must contain at least three unreacted hydroxyl groups if the final compound of this invention is to be represented by the foregoing general formula 2 or 4.

The aforementioned class of terminally unsaturated carboxylic acids contains from 3 up to 20 or more carbon atoms. Representative members of this class include acrylic acid, 3-butenoic acid, 9-decenoic acid and 4-allylbenzoic acid.

A third embodiment of the present compounds, referred to hereinafter as C, is one wherein $R^1$ of the foregoing general formula is $CH_2=CHR^6OR^7$, and $R^4$ is $CH_2=CHR^6OR^{10}<$. The radicals represented by $R^6$, $R^7$ and $R^{10}$ are defined in the preceding paragraphs. Preferably $R^6$ is an alkylene containing from 1 to 10 carbon atoms and $R^7$ is alkylene or hydroxyl substituted alkylene. *

In embodiment C, $R^1$ and $R^4$ represent the residues remaining following removal of one and two hydroxyl groups, respectively, from the saturated polyhydric alcohol or polyhydric phenol portion of an ether derived from that alcohol or phenol and a terminally unsaturated alcohol or phenol containing one or more hydroxyl groups. Preferably the unsaturated alcohol or phenol is monohydric. The saturated polyhydric alcohol or phenol can be any of those discussed hereinabove in connection with embodiments A and B, and the terminally unsaturated alcohol or phenol can likewise be any of those discussed hereinabove in addition to allyl alcohol. In an alternative of embodiment C, two hydroxyl groups of a trihydric alcohol such as 1,1,1-trimethylol propane are reacted with a terminally unsaturated alcohol such as allyl alcohol to form the terminally unsaturated organic compound. In this alternative embodiment $R^1$ is represented by the foregoing general formula $(CH_2=CHR^6O)_2R^{10}-$.

In the fourth embodiment of the present compounds, referred to hereinafter as D, $R^1$ of the foregoing general formulae 1 and 3 is defined as $CH_2=CHR^6OC(O)R^8-$ and $R^4$ of formulae 2 and 4 is defined as $CH_2=CHR^6OC(O)R^8R^{10}<$. In embodiment D, $R^8$ represents a hydrocarbylene radical selected from the same group as previously defined for $R^6$. Preferably $R^7$ represents alkylene containing from 1 to 10 carbon atoms and $R^8$ represents alkylene containing from 1 to 10 carbon atoms, phenylene, hydroxyl-substituted phenylene or methoxy substituted phenylene.

The $R^1$ and $R^4$ substituents of the embodiment D represent the residues remaining following removal of one and two hydroxyl groups, respectively, from the saturated or aromatic hydroxycarboxylic acid portion of an ester derived from that hydroxycarboxylic acid and any of the terminally unsaturated alcohols discussed in connection with the preceding embodiments of the present compounds. It will be understood that the hydroxycarboxylic acid must contain two or more hydroxyl groups per molecule to prepare a compound of this invention corresponding to general formula 2 or 4.

Hydroxcarboxylic acids useful for preparing compounds of embodiment D include but are not limited to hydroxyacetic acid, lactic acid and the isomeric hydroxybenzoic, dihydroxybenzoic and dihydroxycinnamic acids.

Organosilicon compounds corresponding to any of the four embodiments (A–D) of this invention can be prepared by reacting an alkoxysilane of the general formula $(R^2O)_{4-p}R^3{}_pSi$ 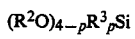 Formula 14 or an alpha,omega-bis-trialkoxysilylhydrocarbon of the general formula $(R^2O)_3SiR^5Si(R^2O)_3$  Formula 15 with one of the terminally unsaturated, hydroxylated organic compounds described in the preceding paragraphs. These organic compounds include terminally unsaturated alcohols, ethers derived from a terminally unsaturated alcohol and a saturated polyhydric alcohol, esters derived from a terminally unsaturated carboxylic acid and a saturated polyhydric alcohol, and esters derived from a terminally unsaturated alcohol and a hydroxycarboxylic acid.

The reaction between the organic and organosilicon compounds described hereinbefore in connection with the various embodiments of the present compounds is conducted under conditions that are typical for condensation reactions involving alkoxysilanes and hydroxlated organic compounds. These reactions are usually conducted under an anhydrous atmosphere such as nitrogen at temperatures from ambient to 200° C. and may employ a catalyst. Useful catalysts include organic amines, tin compounds and titanium compounds. Specific catalysts include but are not limited to stannous octoate, dibutyltin dilaurate and titanium compounds such as tetrabutyl titanate, $Ti(OC_4H_9)_4$.

To function effectively the quantity of catalyst present must be soluble in the reaction mixture. The weight of catalyst typically constitutes from about 0.1 to about 5 percent of the combined weight of all reactants.

Reactions involving replacement of silicon-bonded alkoxy groups generate the alcohol corresponding to the alkoxide group as a by-product under neutral or acidic conditions. Because these reactions are often reversible, it is usually desirable to remove this by-product alcohol by distillation as the reaction progresses. The course of the reaction can then be readily followed by measuring the amount of alcohol collected. Because methanol and ethanol are the lowest boiling alcohols, it is preferable that the alkoxy groups of the present organosilicon reactants, represented by $OR^2$ in the foregoing formulae 1–4 be methoxy or ethoxy.

The reactants and catalyst are preferably heated at a temperature of from about 50° to 200° C. for a period of time sufficient to achieve a substantially complete reaction, as indicated by the amount of by-product alcohol collected. This time period is typically from 1 to about 5 hours.

Some of the ethylenically unsaturated organic reactants used to prepare the compounds of this invention will polymerize at the temperatures used to react them with the organosilicon compound. It may therefore be desirable to include in the reaction mixture an effective amount of a free radical scavenger such as hydroquinone to completely suppress or at least inhibit polymerization of the organic compound during preparation of the present compounds.

Those products of this invention having boiling points below about 200° C. under ambient or reduced pressure can be isolated by distilling the product from the reaction mixture. Higher boiling products can be isolated using known chromatographic techniques with gases or liquids as the carrier.

For some end use applications of the present compounds, such as primers and adhesion promoters, the reaction mixture in which the compound is prepared can be used directly without isolation or purification of the compound.

In some instances it may be desirable to include in the reaction mixture a liquid diluent that may also function as a solvent for the reactants. Suitable diluents include aliphatic and aromatic hydrocarbons that are liquid at ambient temperature and boil within the range of from 50° to about 250° C. Representative diluents include hexane, heptane and liquid aromatic hydrocarbons such as benzene, toluene and xylene.

An alternate method for preparing the compounds of this invention involves reacting one of the terminally unsaturated organic compounds described hereinbefore with an organosilicon compound corresponding to the foregoing general formula 13 or 14, with the exception that one of the alkoxy groups is replaced with a chlorine atom. The reaction is typically conducted in the presence of a suitable acid acceptor. The acceptor can be an organic amine such as pyridine.

The compounds of this invention contain two different classes of reactive groups, namely a terminal carbon-to-carbon double bond and at least two silicon-bonded alkoxy groups. Compounds of this type are suitable for a variety of known end uses, including moisture activated crosslinking and chain extending agents for hydroxyl containing polyorganosiloxanes.

The present compounds will react in the presence of moisture and a suitable catalyst to yield elastomeric or resinous materials, depending upon the nature of the particular compound and other reactive materials present in the composition.

Compounds of this invention wherein $R^2$ and $R^3$ of the foregoing formulae 1–4 are methyl, $R^5$ is ethylene, n is 1 or 2, p is 0 or 1 and r is 0 constitute a preferred class of compounds that are particularly useful as either primers or adhesion promoters for achieving cohesive bonding of polyorganosiloxane resins and elastomers to many inorganic substrates, including glass, steel and aluminum, and to some organic polymers, particularly the class often referred to as engineering thermoplastics. This class includes polyamides such as poly(hexamethylene adipamide), polyesters such as poly(ethylene terephthalate), polyimides and polysulfones.

Polyorganosiloxane compositions that are curable by a variety of means to yield elastomers and resins are well known. Room temperature curable compositions can be of two main types, namely one part compositions curable in the presence of atmospheric moisture and two part compositions curable by a hydrosilation reaction in the presence of a platinum group metal or a compound thereof.

One part room temperature curable polyorganosiloxane compositions typically contain a hydroxyl terminated polydiorganosiloxane with an average of 50 or more repeating units per molecule and a crosslinking agent that is typically a silane containing at least three silicon-bonded alkoxy or other hydrolyzable groups per molecule. A catalyst such as a compound of tin or titanium is usually present to accelerate the curing reaction.

Two part polyorganosiloxane compositions that are curable at room temperature can contain a liquid or solid polydiorganosiloxane having at least two ethylenically unsaturated radical such as vinyl per molecule in combination with a crosslinking agent that is typically an organosilicon compound containing at least three silicon-bonded hydrogen atoms per molecule. A small amount of platinum or a platinum compound is usually also present in these compositions as a hydrosilation catalyst.

Polyorganosiloxane compositions that cure at elevated temperatures can contain a polydiorganosiloxane in liquid or solid form in addition to an organic peroxide.

The aforementioned two part platinum catalyzed polyorganosiloxane compositions that ordinarily cure at room temperature can be modified to cure only when heated by including in the composition one of the known platinum catalyst inhibitors. One such class of inhibitors are the acetylenic alcohols such as 2-methyl-3-butyn-2-ol.

The curable polyorganosiloxane compositions suitable for use in combination with the compounds of this invention as primers or adhesion promoters can contain any of the ingredients conventionally present in these compositions, including fillers, pigments and flame retardants.

Curable polyorganosiloxane compositions are sufficiently described in the literature that a detailed discussion of these compositions in this specification is not required.

The present adhesion promoters are typically added to a curable polyorganosiloxane composition in amounts of from 0.1 to about 10 percent by weight, based on the weight of the total composition. The adhesion promoters are particularly effective in combination with polyoganosiloxane compositions that are cured by a hydrosilation reaction at room temperature.

When used as primers at least one member from the aforementioned class of preferred compounds of this invention is applied as a thin film to at least one of the surfaces to be bonded. The compounds can be diluted in a suitable solvent to facilitate their application to a substrate. Solvents for the present preferred class of compounds include liquid hydrocarbons such as heptane, benzene, toluene and xylene, and the methyl and ethyl ethers of either ethylene glycol or propylene glycol.

Cohesive bonding of polyorganosiloxane elastomers or resins to amorphous or 'glassy' organic polymers such as polymerized esters of acrylic or methacrylic acids, polycarbonates and polystyrene can be achieved by using the aforementioned preferred class of the present compounds as primers in combination with copolymers derived from 1) at least one ethylenically unsaturated organic monomer such as styrene and esters of methacrylic or acrylic acid, and 2) a silane of the general formula $$RSiX_3 \qquad \text{Formula 17}$$

where R represents vinyl, allyl, or $CH_2=CR'C(O)OR''$, R' is methyl or hydrogen, R'' is alkyl containing from 1 to 4 carbons, and X represents a hydrolyzable group such as halogen, or lower alkoxy such as methoxy. These copolymers are disclosed in U.S. Pat. No. 3,306,800 that issued to E. Plueddemann on Feb. 26, 1967 and is incorporated herein by reference as a teaching of primers that are suitable for use in combination with the present adhesion promoters.

A particularly preferred class of copolymers is derived from methyl methacrylate and 3-methacroloxypropyltrimethoxysilane. The methyl methacrylate constitutes from 5 to about 95 weight percent of the monomer mixture, preferably from 80 to 95 weight percent.

The primer composition also contains a crosslinking agent for the copolymers. Suitable crosslinking agents include organohydrogensiloxanes containing an average of at least three silicon-bonded hydrogen atoms per molecule.

A mixture containing one or more of the copolymers described in the immediately preceding paragraphs, one or more of the preferred compounds of this invention and a crosslinking agent is applied as a primer to at least one of the surfaces to be bonded. Alternatively, one of the preferred compounds of this invention is blended together with a curable polyorganosiloxane composition, and the copolymer and crosslinking agent are applied as a thin film to at least one of the surfaces to be bonded.

The following examples describe preferred embodiments of the present compounds and demonstrate their utility as adhesion promoters and primers for polyorganosiloxane compositions. The examples should not be interpreted as limiting the scope of this invention as defined in the accompanying claims. All parts and percentages disclosed in the examples are by weight unless otherwise indicated.

The general method used to prepare the exemplified compounds was to heat a mixture containing a terminally unsaturated organic reactant, an organosilicon compound and 1 percent of tetrabutyl titanate, based on the total weight of the reaction mixture, in a reactor equipped to condense and isolate liquid that vaporized from the reaction mixture. Heating of the reaction mixture was continued until the temperature of the reaction mixture reached between 100° and 110° C. for the silane reactants or from 110° to 166° C. for 1,2-bis(trimethoxysilyl)ethane. The amount of by-product alcohol, either methanol or ethanol, recovered during this heating period was substantially equal to the calculated value based on the amounts of organosilicon and organic compounds present.

The organosilicon compounds used were tetramethoxysilane, tetraethoxysilane, methyltrimethoxysilane, phenyltrimethoxysilane, and 1,2-bis(trimethoxysilyl)ethane. Reaction mixtures containing the four silanes were heated until the temperature of the reaction mixture reached a value within the range from 100° to 110° C. to prevent excessive distillation of silane from the reaction mixture. Reaction mixtures containing bis(trimethoxysilyl)ethane could be heated to 160° C. Without substantial loss of this reactant by distillation.

EXAMPLE 1

Compounds of this invention were prepared by combining a terminally unsaturated organic compound, an organosilicon compound containing at least three silicon-bonded methoxy or ethoxy groups per molecule and 1%, based on the total weight of the reaction mixture, of tetrabutyl titanate. The resultant mixture was heated with stirring while removing volatile materials by distillation. Heating was continued until an amount of alcohol equivalent to a substantially complete reaction was isolated from the reaction mixture.

The types and molar ratios of reactants and the final temperature of the reaction mixture are listed in Table 1. The reactants used are represented by the following abbreviations. Unless otherwise indicated, the final temperature of the reaction mixture was within the range from 100° to 110° C.

ORGANIC REACTANTS

U: 10-undecenol
E: Eugenol
HEA: Hydroxyethyl acrylate
HPA: Hydroxypropyl acrylate
MATMP: Monoallyl ether of 1,1,1-trimethylolpropane
DATMP: Diallyl ether of 1,1,1-trimethylolpropane
PB: A hydroxyl endblocked polybutadiene corresponding to the average formula

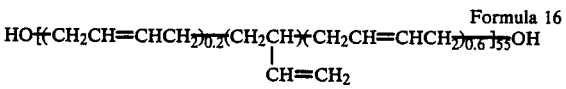

Formula 16

This polymer is available as Poly BD R-45M from Arco Chemicals.
AE: 2-Allyloxy-1-ethanol
AP: o-Allylphenol.

ORGANOSILICON REACTANTS

TMS: Tetramethoxysilane
MTMS: Methyltrimethoxysilane
PTMS: Phenyltrimethoxysilane
TES: Tetraethoxysilane
TMSE: 1,2-bis(trimethoxysilyl)ethane.

TABLE 1

| Product No. | Reactants | Molar Ratio of Reactants | Final Reaction Temperature |
|---|---|---|---|
| 1 | U/TMS | 1/1 | |
| 2 | E/TMS | 1/1 | |
| 3 | HPA/TMS* | 1/1 | |
| 4 | MATMP/TMS | 1/1 | |
| 5 | MATMP/MTMS | 1/1.1 | 120° C. |
| 6 | MATMP/MTMS | 1/2.2 | 110° C. |
| 7 | MATMP/TES | 1/1 | |
| 8 | MATMP/PTMS | 1/1 | |
| 9 | PB/MTMS | 1/1 | |

TABLE 1-continued

| Product No. | Reactants | Molar Ratio of Reactants | Final Reaction Temperature |
|---|---|---|---|
| 10 | AE/MTMS | 1/1 | |
| 11 | E/MTMS | 1/1 | |
| 12 | AP/MTMS | 1/1 | |
| 13 | MATMP/TMSE | 1/2 | 150° C. |
| 14 | DATMP/TMSE | 1/1 | 160° C. |
| 15 | HEA/MTMS* | 1/1 | |

*0.004% of hydroquinone was added to the reaction mixture as a polymerization inhibitor
**100–110° C. unless otherwise specified

EXAMPLE 2

This example demonstrates the efficiency of representative compounds of this invention as adhesion promoters for cohesively bonding a polyorganosiloxane elastomer to glass and metal substrates. A curable, pumpable polyorganosiloxane composition was prepared by blending the following ingredients to homogeniety:

101.3 parts of a dimethylvinylsiloxy endblocked polydimethylsiloxane having a viscosity of about 3 Pa.s at 25° C.;

34.7 parts of a benzene soluble resinous copolymer containing triorganosiloxy units and $SiO_2$ units in the mol ratio of about 0.7 mol of triorganosiloxy unit per mol of $SiO_2$ unit where the triorganosiloxy units are trimethylsiloxy units and dimethylvinylsiloxy units and the copolymer contains from 1.4 to 2.2 weight percent of silicon-bonded vinyl radicals;

48.9 parts of fume silica;

0.7 part of water;

0.31 part of a hydroxyl terminated polydiorganosiloxane containing dimethylsiloxane and methylvinylsiloxane units about 10 weight percent vinyl radicals and about 16 weight percent hydroxyl radicals;

8.14 part of hexamethyldisilazane;

5.28 parts of a trimethylsiloxy endblocked polydiorganosiloxane having an average of five methylhydrogensiloxane units and three dimethylsiloxane units per molecule with a silicon-bonded hydrogen atom content in the range of 0.7 to 0.8 weight percent;

0.15 part of a curing catalyst in the form of a chloroplatinic acid complex of divinyltetramethyldisiloxane that had been diluted with a liquid dimethylvinylsiloxy terminated polydimethylsiloxane to achieve 0.7 weight percent platinum; and 0.015 part of 2-methyl-3-butyne-2-ol as a catalyst inhibitor.

Samples of this composition were blended with 1 percent by weight of compounds 1-5 and 7-12 listed in the foregoing Table 1. A 3.2 mm-thick layer of the resultant composition was applied as a 2.5 centimeter-wide strip to a glass microscope slide, to sheets of cold-rolled steel and aluminum, and to brass shim stock. The coated substrate was cured for from 5 to 7 minutes at a temperature of 150° C.

The adhesion of the elastomer to the substrate was evaluated by loosening one of the 2.5 cm.-wide edges of the cured coating with a razor blade. A weight of about 0.1 kilogram was attached to this loosened edge strip and allowed to hang free in an attempt to peel the remainder of the coating from the substrate. The coated surface was maintained in a substantially horizontal plane and the amount of weight was gradually increased to 10 kilograms, If the coating separated from the substrate, the weight (i.e. the force) being applied at the time of failure was recorded, and the failure was rated an adhesive one. Coatings which could not be peeled from the substrate under a force of 10 kg. were rated as being cohesively bonded to the substrate.

A substrate coated with a cured elastomer prepared as described in the preceding paragraph but which did not contain an adhesion promoter was used as a control. The amount of force, i.e. the amount of weight attached to the coating, being applied at the time separation of the coating from the substrate occurred was 0.9 kg. for glass, 0.1 kg. for cold rolled steel, 0.2 kg. for aluminum and 0.5 kg. for brass.

All of the elastomers with the exception of the one prepared using compound 7 from the preceding Table 1 exhibited cohesive bonding to all substrates. The elastomer prepared using compound 7 was cohesively bonded to glass and brass, but separated from cold rolled steel and aluminum under applied weights of 2.5 and 1.6 kg., respectively, which represented a significant improvement over the control. In all instances the weight required to achieve peeling of the control coating from the substrate was less than one kilogram.

EXAMPLE 3

This example demonstrates the performance of a primer composition containing one of the preferred compounds of this invention in combination with a known primer for adhering inorganic reinforcing agents to organic polymers.

The primer was prepared by homogeneously blending 2 parts of compound 15 from Table 1 of the preceding Example 1, 10 parts of a 20 percent solution in ethyl acetate of a methyl methacrylate/3-methacryloxypropyltrimethoxysilane copolymer, 87 parts of the monomethyl ether of propylene glycol, and 1 part of a trimethylsiloxy endblocked polymethylhydrogensiloxane having a viscosity of about 0.13 Pa.s at 25° C. and a silicon-bonded hydrogen atom content of about 1.6 percent by weight.

The copolymer was prepared by reacting methyl methacrylate and 3-methacryloxypropyltrimethoxysilane in a molar ratio of 10:1, respectively, in the presence of 1 percent by weight, based on total monomers, of 3-mercaptopropyltrimethoxysilane and a catalytic amount of benzoyl peroxide. The polymerization was conducted in ethyl acetate.

The ability of the primer to cohesively bond a polydimethylsiloxane elastomer to both polymethyl methacrylate and a polycarbonate was evaluated using a modification of ASTM test procedure No. D 1002.

Samples of polymethyl methacrylate (A) and a polycarbonate (B) in sheet form were cleaned by wiping them with hexane followed by a wiping with methanol. The samples measured 2.5 cm in width and 7.6 cm in length. After the samples had dried, a film of the primer composition was applied by wiping with a clean cloth. The samples were then allowed to air dry for 20 minutes before a second coating of primer was wiped on in the same manner as the first coat. After drying in air for 90 minutes, a 2.7 cm.-wide strip of curable polymethylsiloxane elastomer was applied to one end of the primed surface either sample A or B. One end of the primed surface of the other sample was placed in contact with opposite surfaces of the elastomer layer to achieve an overlap of 2.5 cm. between the polycarbonate and polymethylmethacrylate samples. The elastomer was curable by a platinum catalyzed hydrosilation reaction and exhibited a durometer of 50 on the Shore A scale following curing.

The laminate of polycarbonate and polymethyl methacrylate samples separated by the layer of cured elastomer was placed in a jig that maintained the thickness of the elastomer layer at 1.3 mm during curing. The resultant assembly was then placed between the platens of a press that was heated to a temperature of 100° C. The platens of the press were adjusted to maintain a pressure of 345 KPa on the sample for two hours. The assembly was then removed from the press and allowed to equilibrate under ambient conditions for at least 16 hours prior to being tested.

Testing of the samples to determine the strength and nature of the bond between the elastomer and the two organic polymers was conducted under the conditions specified in ASTM test procedure No. D 1002. The load at failure and the type of failure were noted. The three samples tested failed at loads of 2622, 2746 and 2863 kPa. In all instances the failure was cohesive, i.e., the elastomer tore while retaining adhesion to both substrates over the entire contact area.

That which is claimed:

1. A primer composition for adhering a curable polyorganosiloxane elastomer composition to an inorganic substrate, said primer composition comprising an organosilicon compound having a general formual selected from the group consisting of $(R^1O)_n(R^2O)_{4-n-p}R^3_pSi$, $R^4[OSi(OR^2)_{3-p}R^3_p]_2$, $(R^1O)_n(R^2O)_{3-n}SiR^5Si(OR^1)_2(OR^2)_{3-n}$, and $R^4[OSi(OR^2)_2R^5Si(OR^2)_3]_2$, where $R^1$ represents a radical selected from the group consisting of $CH_2=CHCH_2R^6—$, $CH_2=CHR^6OR^7—$, $CH_2=CHR^6OC(O)R^8—$, $CH_2=CHR^9C(O)OR^7—$, and $(CH_2=CHR^6O)_2R^{10}—$;

$R^2$ and $R^3$ are methyl;

$R^4$ represents a radical selected from the group consisting of $CH_2=CHR^{10}<$, $CH_2=CHR^6OR^{10}<$, $CH_2=CHR^6OC(O)R^{10}=$ and $CH_2=CHR^9C(O)OR^{10}=$;

$R^5$ represents ethylene;

$R^6$ represents a hydrocarbylene or substituted hydrocarbylene radical where the substituent is hydroxyl or alkoxy;

$R^7$ is selected from the same group as $R^6$ or represents an allyloxy-substituted hydrocarbylene radial, with the proviso that $R^7$ contains at least 2 carbon atoms;

$R^8$ is selected from the same group as $R^6$;

$R^9$ represents a single bond or a radical selected from the same group as $R^6$;

$R^{10}$ represents a trivalent hydrocarbon radical;

n is 1 or 2;

p is 0 or 1; r is 0 or 1; and 4−n−p is at least 2.

2. A primer composition according to claim 1 where $R^6$ is alkylene, phenylene, alkoxy substituted phenylene or the residue remaining following removal of one terminal hydroxyl group from a hydroxyl terminated polybutadiene having an average degree of polymerization of between 50 and 60.

3. A compound according to claim 1 where $R^1$ is $CH_2=CHR^6OR^7—$, $R^6$ is methylene and $R^7$ is

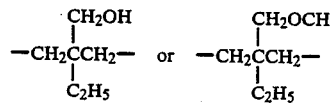

4. A primer composition according to claim 1 where $R^1$ is $CH_2CHR^6OC(O)R^8$, where $R^6$ represents alkylene containing from 1 to 10 carbon atoms, and $R^8$ represents alkylene containing from 1 to 10 carbon atoms, phenylene, hydroxyl substituted phenylene or methoxy substituted phenylene.

5. A primer composition according to claim 1 where $R^1$ is $CH_2=CHR^9C(O)OR^7—$, and where $R^9$ represents a single bond and $R^7$ represents alkylene containing from 2 to 10 carbon atoms, hydroxyl substituted alkylene containing from 3 to 10 carbon atoms or phenylene.

6. A primer composition according to claim 1 where $R^1$ is $(CH_2=CHR^6O)_2R^{10}$, $R^6$ is methylene and $R^{10}$ is

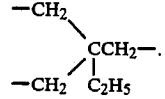

7. A primer composition according to claim 1 where $R^4$ is $CH_2=CHR^{10}$, where $R^6$ is methylene and $R^{10}$ is

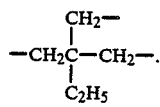

8. A primer composition according to claim 1 where said primer includes a copolymer consisting essentially of from 10 to 95 weight percent of repeating units derived from 3-(methacryloxypropyl)trimethoxysilane and from 5 to 90 percent by weight of repeating units derived from methyl methacrylate.

9. A primer composition according to claim 8 where said silane constitutes from 40 to 60 weight percent of the combination of said compound and said copolymer.

10. A primer composition according to claim 9 where said organosilicon compound exhibits the general formula $CH_2=CHR^6OR^7—$ or $(CH_2=CHR^6O)_2R^{10}$ where $R^6$ is methylene, $R^7$ is

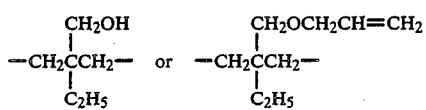
and $R^{10}$ is
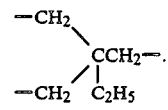
* * * * *